(12) United States Patent
Aelony et al.

(10) Patent No.: US 10,568,743 B2
(45) Date of Patent: Feb. 25, 2020

(54) ANKLE REPLACEMENT APPARATUS AND METHOD

(71) Applicant: NDSU Research Foundation, Fargo, ND (US)

(72) Inventors: Jared S. Aelony, Detroit Lakes, MN (US); Fardad Azarmi, Fargo, ND (US); Chad A. Ulven, Walcott, ND (US)

(73) Assignee: NDSU Research Foundation, Fargo, ND (US)

( * ) Notice: Subject to any disclaimer, the term of this patent is extended or adjusted under 35 U.S.C. 154(b) by 0 days.

(21) Appl. No.: 14/888,617

(22) PCT Filed: May 1, 2014

(86) PCT No.: PCT/US2014/036399
§ 371 (c)(1),
(2) Date: Nov. 2, 2015

(87) PCT Pub. No.: WO2014/179589
PCT Pub. Date: Nov. 6, 2014

(65) Prior Publication Data
US 2016/0074169 A1   Mar. 17, 2016

Related U.S. Application Data

(60) Provisional application No. 61/818,160, filed on May 1, 2013.

(51) Int. Cl.
*A61F 2/42* (2006.01)
*A61F 2/30* (2006.01)
(Continued)

(52) U.S. Cl.
CPC ........ *A61F 2/4202* (2013.01); *A61F 2/30767* (2013.01); *A61F 2/42* (2013.01);
(Continued)

(58) Field of Classification Search
CPC .. A61F 2/42; A61F 2/4202; A61F 2002/4205; A61F 2002/30364; A61F 2002/4207; A61F 2/3868
See application file for complete search history.

(56) References Cited

U.S. PATENT DOCUMENTS 8,328,874 B2 * 12/2012 Lee .................. A61F 2/3868
623/20.15
2004/0167631 A1   8/2004 Luchesi et al.
(Continued)

FOREIGN PATENT DOCUMENTS

WO   0069373 A1   11/2000
WO   2005030098 A1   4/2005
(Continued)

OTHER PUBLICATIONS

International Preliminary Report on Patentability and Written Opinion dated Nov. 3, 2015 for corresponding International Application No. PCT/US2014/036399 filed May 1, 2014, 6 pages.
(Continued)

*Primary Examiner* — Dinah Baria
(74) *Attorney, Agent, or Firm* — Merchant & Gould P.C.

(57) ABSTRACT

In some exemplary embodiments, an ankle replacement prosthesis includes a tibial component which provides a convex bearing surface, and a talar component which provides a concave bearing surface configured to interface with the convex bearing surface of the tibial component to provide a joint of the ankle replacement prosthesis. The tibial component is configured to be attached to a patient's tibia and the talar component is configured to be attached to the patient's talus.

13 Claims, 13 Drawing Sheets

(51) Int. Cl.
*A61L 27/16* (2006.01)
*A61L 27/44* (2006.01)

(52) U.S. Cl.
CPC ............. *A61L 27/16* (2013.01); *A61L 27/443* (2013.01); *A61F 2002/3093* (2013.01); *A61F 2002/4205* (2013.01); *A61F 2002/4207* (2013.01)

(56) References Cited

U.S. PATENT DOCUMENTS

| | | | |
|---|---|---|---|
| 2004/0186585 A1 | 9/2004 | Feiwell | |
| 2006/0247788 A1* | 11/2006 | Ross | A61F 2/4202 623/21.18 |
| 2007/0173947 A1* | 7/2007 | Ratron | A61B 17/15 623/21.18 |
| 2008/0243261 A1* | 10/2008 | Wyss | A61F 2/3868 623/20.33 |
| 2011/0035018 A1* | 2/2011 | Deffenbaugh | A61F 2/389 623/20.28 |
| 2011/0035019 A1* | 2/2011 | Goswami | A61F 2/4202 623/21.18 |

FOREIGN PATENT DOCUMENTS

| | | |
|---|---|---|
| WO | 2006136940 A2 | 12/2006 |
| WO | 2011146628 A2 | 11/2011 |
| WO | WO 2013/150308 * | 10/2013 |

OTHER PUBLICATIONS

International Search Report dated Aug. 8, 2014 for corresponding International Application No. PCT/US2014/036399 filed May 1, 2014, 4 pages.
Examination Report from European Patent Office dated May 23, 2018 for European Application No. 14 733 406.4, 6 pages.

* cited by examiner

Von-Mises stress for the two component design without bones in the analysis.

Von-Mises stress for the two component design with bones in the analysis

Von-Mises stress for the hybrid design without bones in the analysis.

Von-Mises stress for the hybrid design with bones in the analysis.

| Material | Compressive Strength (MPa) | Tensile Strength (MPa) | Young's Modulus (GPa) |
|---|---|---|---|
| Titanium Alloy | 750-1200 | 800-1450 | 110-120 |
| CoCrMo Alloy | 760-839 | 1290-1420 | 235-247 |
| UHMWPE | 25.7-33.1 | 38.6-48.3 | 0.894-0.963 |
| Cortical Bone | 145-167 | 86-123 | 18.5-20.5 |
| 30% CFR PEEK | 172-240 | 190-228 | 12.8-24.1 |
| Invibio Motis™ | 200 | 155 | 15 (Tensile) 12 (Compressive) |

Table 1: Material data for traditional implant materials, cortical bone, and 30% CF PEEK, taken from CES Edupack 2011

Fig. 17

ANKLE REPLACEMENT APPARATUS AND METHOD

CROSS-REFERENCE TO RELATED APPLICATION

This application is a Section 371 National Stage Application of International Application No. PCT/US2014/036399, filed May 1, 2014 and published, in English, as WO 2014/179589 A1 on Nov. 6, 2014, which claims priority to U.S. Provisional Patent Application No. 61/818,160, filed on May 1, 2013.

FIELD OF THE INVENTION

The present invention relates to ankle replacement prosthesis and methods of implanting the same.

BACKGROUND OF THE INVENTION

As in the need for hip and knee replacements, patients requiring an ankle replacement no longer have a fully functional ankle. The most common end-stage ankle complications arise from arthritic pain either from old age or previous trauma. For many years, arthrodesis, or ankle fusion, was the primary technique for reducing the pain in patients; however, fusing the ankle bones together greatly reduces the joint's range of motion, and could potentially cause serious alterations in gait, which often leads to additional joint and mobility complications. To many people, having a fully functional ankle is vital in maintaining an active and healthy lifestyle.

In an effort to produce an alternative to arthrodesis, developers began designing and constructing ankle replacement prosthesis in the early 1970s. Throughout the following decades, researchers have yet to design a proven reliable, long lasting replacement. The United States Food and Drug Administration (FDA) approved designs being used in the United States today are the Agility, INBONE, Salto-Talaris, and Eclipse total ankle replacements, which are all two-component designs. A fifth, three-component design called the Scandinavian Total Ankle Replacement was recently approved by the FDA in May 2009. Many more types are available in other countries; mostly in Europe. The ankle replacements available typically contain very similar components: a tibial component, a talar component, and a polyethylene insert that serves as a bearing between the other two components. The most significant differences are how the components are fixed to the tibia and talus, the contour of the bearing-talar component surface, and the type of outer coating applied to the metallic components.

A major issue with current designs on the market is longevity of the prosthesis. Most complications are associated with wound healing, polyethylene bearing wear and fracture, and dislocation of components. Overcoming the high stresses on such small components is the primary challenge for designers. High concentration of stresses at the point of fixation, caused by the transfer of energy through ankle movement, can ultimately cause component loosening and overall prosthesis failure.

Improved ankle replacement prosthesis and methods which address one or more of the above-described problems, or which address other problems or provide other advantages not discussed above, would be a significant improvement in the field of ankle replacement.

The discussion above is merely provided for general background information and is not intended to be used as an aid in determining the scope of the claimed subject matter.

SUMMARY

The summary and the abstract are provided to introduce a selection of concepts in a simplified form that are further described below in the Detailed Description. The summary and the abstract are not intended to identify key features or essential features of the claimed subject matter.

Disclosed embodiments include multiple novel concepts. The shape of the disclosed total ankle replacement (TAR) designs can be used to maximize surface area in contact at all points of motion to provide better stress distribution. Another novel concept includes the snap fit of the bearing component into the tibial component which allows better degree of motion than with strictly a traditional 2 component design. This provides advantages for the patient to provide a more natural degree of rotation, while maintaining the surgical advantages of having the tibial component fixed to the tibia. Having the bearing component fixed to the tibial component while still allowing motion of the bearing component helps to reduce stresses to other joints. As used herein, a bearing or a bearing component can be considered to include weight bearing components and/or components that provide bearing surfaces that are in contact but slide or move relative to one another. Individual components can also provide both bearing functions in some instances. For example, a tibial bearing component can be weight bearing and provide a tibial bearing surface which interfaces and moves relative to a talar bearing component. Other bearing components can slide, pivot or rotate relative to each other.

Another novel aspect of some disclosed embodiments includes fixation of the talar component to the bone in how it is not just done with bony ingrowth, but is also achieved with screws to afford greater stabilization. Yet another novel feature of some disclosed embodiments includes fixation of the tibial component with a shorter barrel design with a cross hole to allow bony ingrowth as opposed to long stems found on other TARs in the market.

Further still, the integration of different materials provides novel features in some embodiments, which has led to at least the following options for exemplary designs:

a. CoCrMo tibial component, UHMWPE bearing, and CoCrMo talar component b. CoCrMo tibial component, CFR PEEK bearing, and CoCrMo talar component c. CFR PEEK tibial component, CFR PEEK bearing, and CFR PEEK talar component Yet another novel feature can include the geometry, rounded contours and the surface properties of each component (e.g., semi-elliptical in shape with a smooth surface) to require little bone to be removed during surgery and less stretching/navigation of the surrounding tendons which allows quicker surgery and faster rehabilitation time.

In some exemplary embodiments, an ankle replacement prosthesis 100; 800 includes a tibial component 120; 720 which provides a convex bearing surface 128, and a talar component 110 which provides a concave bearing surface 428 configured to interface with the convex bearing surface of the tibial component to provide a joint of the ankle replacement prosthesis. The tibial component is configured to be attached to a patient's tibia 220 and the talar component is configured to be attached to the patient's talus 210.

In some exemplary embodiments, the tibial component 120; 720 comprises a tibial bearing component 127 providing the convex bearing surface 128 and a tibial attachment component 121 configured to be attached to the patient's tibia. In some exemplary embodiments, the tibial bearing component and the tibial attachment component are configured to be secured to one another. These components can be secured to one another by a pivotal attachment to allow rotation between the tibial bearing component and the tibial attachment component, allowing for the benefits of a mobile bearing implant while keeping the bearing fixed. The rotation can be about an axis of loading of the ankle replacement prosthesis.

In some exemplary embodiments, the talar component further comprises a plurality of screw receiving apertures 250 each disposed and arranged on the talar component to receive a corresponding one of a plurality of screw fasteners 505 to attach the talar component to the patient's talus. In some exemplary embodiments, at least one of the plurality of screw receiving apertures is disposed and arranged so as to direct the corresponding one of the plurality of screw fasteners toward the talar neck 212 of the patient's talus in order to maximize screw length. In some exemplary embodiments, the talar component has a concave middle portion and a flat outer edge portion, and at least one of the plurality of screw receiving apertures is disposed at an angle relative to the flat outer edge portion of between 50 degrees and 60 degrees, with an angle of 55 degrees having been found to be particularly beneficial. There is at least one of the plurality of screw receiving apertures can be disposed and arranged so as to direct the corresponding one of the plurality of screw fasteners toward the talar neck, for example from posterior to anterior.

In some exemplary embodiments, the tibial component includes a cylinder member 122 extending in a first direction 123 and configured to be inserted into the patient's tibia. The cylinder can include at least one cross aperture 725, extending in a direction with a directional component which is orthogonal to the first direction, to allow bony ingrowth of the tibia into the cylinder member of the tibial component. In some exemplary embodiments, the first direction 123 in which the cylinder member 122 extends is orthogonal to an axis of loading 105 of the ankle replacement prosthesis.

In some exemplary embodiments, the tibial component and talar component comprise carbon-fiber-reinforced (CFR) polyetheretherketone (PEEK), and the bearing surfaces of the tibial component and the talar component comprise ultra-high-molecular-weight polyethylene (UHMWPE).

The above described features and embodiments can be used in any combination with each other, whether specifically illustrated as such or not, and disclosed embodiments should be interpreted to include all such combinations and variations.

BRIEF DESCRIPTION OF THE DRAWINGS

FIG. 17 is a table showing material properties of various implant materials for the disclosed prostheses.

DETAILED DESCRIPTION

Figure 1:
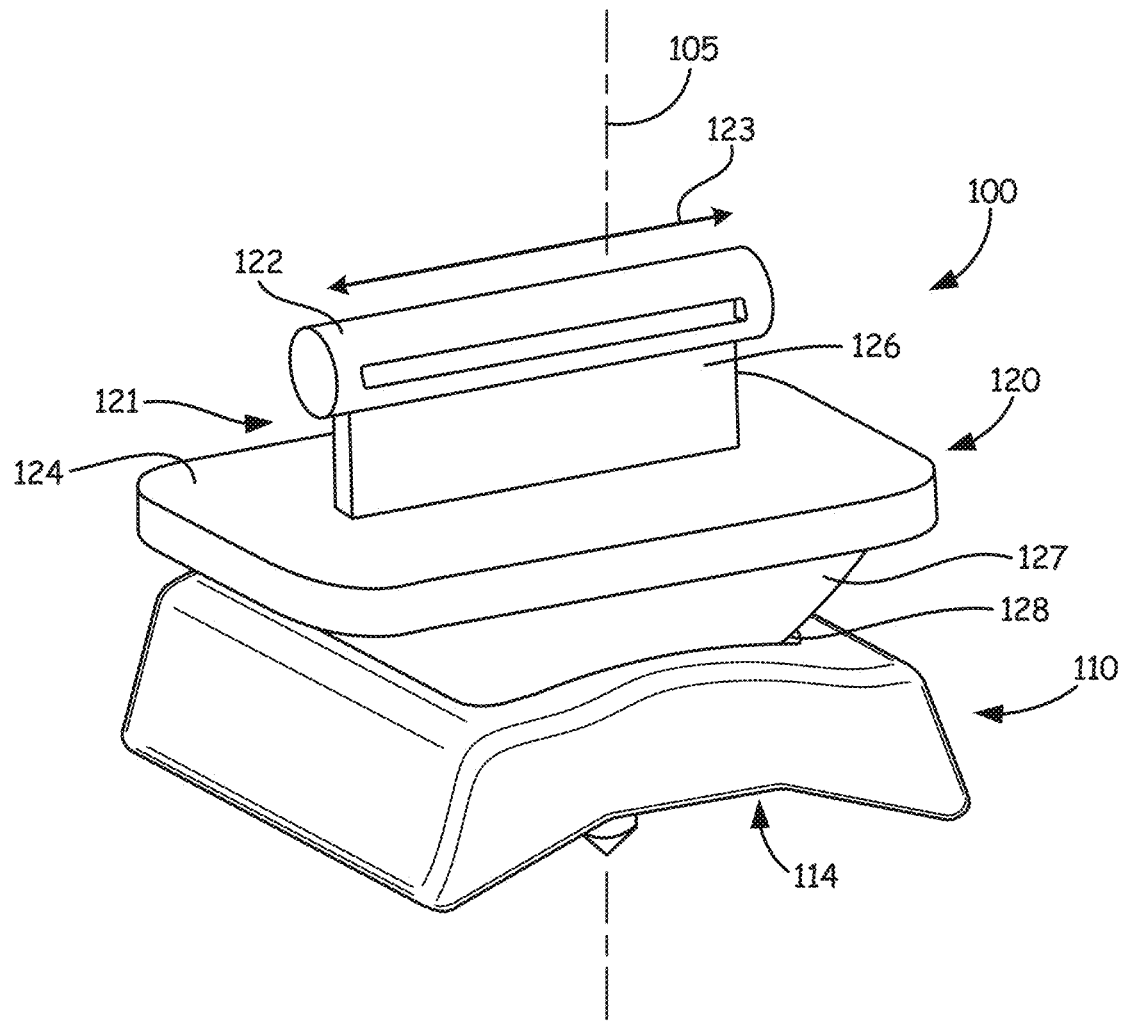
FIG. 1 is a perspective view of an embodiment of a total ankle replacement (TAR) prosthesis.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "coupled" and variations thereof are used broadly and encompass both direct and indirect connections and couplings. Further, "connected" and "coupled" are not restricted to physical or mechanical connections or couplings.

Anatomy of the Ankle

When designing a prosthetic, the first thing the designer wants to do is understand how that part of the human body works. The prosthetic should function as closely as possible to the portion of the body it is replacing. Understanding this criterion, research of the anatomy of a human ankle was used to provide disclosed embodiments.

The ankle joint acts as a hinge. It has to pivot the foot both up and down, as well as a small degree left and right. The upward motion is called dorsiflexion, while the downward motion is referred to as plantar flexion. The rotation in the transverse plane is called abduction (external rotation) or abduction (internal rotation).

The pivoting motion is achieved by the socket that is formed between the talus and the lower portion of the fibula and tibia. The tibiotalar joint is a synovial joint, which is a joint filled with synovial fluid. The tibia is located on the medial side of the leg and has a larger cross-section than the fibula. The tibia is also in line directly between the femur and the talus and therefore caries the most load. The talus is the only bone that articulates with the fibula and tibia. The talus features a domed head, a neck, and rectangular body. The contact surface between the bones, or the bearing surface, is lubricated by the articular cartilage. This cartilage is approximately one-quarter of an inch, and allows the bones to move smoothly, while acting as a shock absorber when walking or running. Cartilage can have a coefficient of friction as low as $\mu=0.002\mu=0.0026$.

Due to the geometry of the talar dome, the axis of rotation is a constantly changing one. More specifically, the media profile is compounded of the arcs of two circles of differing radii causing the axis of rotation to vary. The axis of the ankle passes through the center of these two circles. It has been found that the average radius of the talar dome is about 20 mm. This type of motion allows the talus to glide and slide. The normal range of motion in the ankle ranges from 23 to 56 degrees of plantarflexion and from 13 to 33 degrees of dorsiflexion while the transverse rotation is found to be between 6 to 12 degrees. For purposes of discussion of disclosed exemplary embodiments, the ankle will be considered to act as a simple hinge.

Forces in the Ankle Joint

It is widely agreed upon by researchers and doctors that the compressive force the ankle endures is estimated to be approximately four times body weight during normal walking. The ankle has a load bearing surface of approximately 12 $cm^2$. Of that area, only about 7 $cm^2$ accounts for the tibio-talar contact area. With this information, it can be determined that in a person weighing 900 N (about 200 lbs) their ankle would experience a compressive load per unit area of approximately 5.1 MPa. In addition to walking, it has been found that jumping could generate anywhere from two to twelve times body weight while running at 4.5 m/s generated a force of 2.8 times body weight.

Mechanical Properties of Bone

The mechanical properties were researched in order to perform finite element analysis and to aid in the selection of alternative implant materials. There are two types of bone: trabecular and cortical. Trabecular bone is porous and is filled with fatty viscous fluid called marrow. Cortical bone is dense and makes up the outer layer of bone while. In areas of articulating surfaces, cortical bone is typically thicker in order to support the transmitted load. Studies have also shown that the cortical bone of the talus is 40% stronger than the cortical bone the above talus; therefore, it is vital to retain as much of the talar dome as possible in total ankle replacements.

Actual tensile and compressive strengths of bone vary greatly from bone to bone and from person to person. For this report, the compressive strength and Young's Modulus of cortical bone will be considered to be 159 MPa and 18.1 GPa, respectively. The compressive strength and Young's Modulus of trabecular bone will be considered to be 1.068 MPa and 0.28 GPA, respectively.

Current Total Ankle Replacements

Most of the total ankle replacements (TARs) currently being implanted are of the two or three-component design. A two-component design consists of a talar component and a tibial component, with the bearing surface being fixed to the tibial component. A three-component design also has the talar component and the tibial component, but the bearing surface is its own separate entity, floating between the tibial and talar components. The two-component designs include the Agility, INBONE, Salto-Talaris, and Eclipse TARs, while the Scandinavian Total Ankle Replacement (STAR) is a three-component design.

Reason of Failure of TARs

The current TAR designs only have between a 75-80% survival rate after 10 years. This compares to a total knee replacement survival rate of 80% after 20 years. There are two main contributors to the higher rate of failure of the TAR compared to a total knee replacement. First, the ankle receives forces that are approximately four times a person's body weight when walking, or almost twice the amount of force a knee receives during the same movement. Second, the ankle has only approximately half the joint surface area as the knee does. The large forces imposed on the ankles small surface area, as well as some surgical missteps, result in a few main complications that also may result in complete TAR failure.

The most common mode of failure is shifting, which includes subsidence into the talus, of the prosthesis. This occurs when the supporting bone becomes weak from repetitive loading or osteolysis. Another mode of failure is premature wearing of the bearing surface. This is caused by repetitive loading as well the high wear rate of current materials used. Most other complications occur during surgery, and include deep infection of the prosthesis, major wound breakdown, and tibial nerve injury.

Current Materials Selection

Most TARs are currently made of two materials. The talar and tibial components are made of a cobalt chromium alloy. This is the same metal used in knee/hip replacements. It is chosen because of its high strength, corrosion resistance and bio-compatibility. The second material used is ultra-high-molecular-weight-polythylene (UHMWPE). This material is used between the tibial and talar components as the bearing surface and is chosen because of its low coefficient of friction and its relative toughness.

Hydroxyapatite

Hydroxyapatite is a naturally occurring mineral form of calcium apatite and is one of the few materials to be considered bioactive. It is found in human bones and teeth and is commonly used as filler for to replace amputated bone and teeth. In orthopedics, it is used to promote bone growth. A study in 1998 investigated the fixation abilities of hydroxyapatite implants with porous and grit-blasted surface textures. Both devices were implanted into the femurs of eight dogs. The study concluded that implants with porous surface textures coated with hydroxyapatite perform better than the grit blasted surface texture with hydroxyapatite. Using a porous coating with hydroxyapatite can therefore allow a more stable prosthesis fixation and ultimately prolong the implant's life.

Design Process

Design Constraints

In development and evaluation of disclosed embodiments, a set of constraints were developed in order to define the boundaries of the design process. The set included three categories: engineering, environmental, and budgetary. The following constraints were used in the design process and in determining a final design.

Engineering Constraints

There are multiple engineering constraints that are ideally addressed to ensure a safe and extended implant life:

Implant Longevity:

The first of which, and of significant importance, is the life expectancy of the prosthesis successfully implanted into a patient. Currently, the majority of ankle replacements last an average of 10 years. In exemplary embodiments, disclosed prosthetic designs outlast this length of time. Materials are selected that can withstand the loads and movements subjected upon it in everyday life. ASTM standards F 732-00—"Standard Test Method for Wear Testing of Polymeric Materials used in Total Joint Prosthesis" and G 99-05—"Standard Test Method for Wear Testing with a Pin-on-Disk Apparatus" were be used to test material properties.

Biocompatibility:

Not only do materials meet strength and flexural requirements in exemplary embodiments, but they also conform to biocompatibility standards to avoid rejection from the body. Materials were chosen such that the elastic moduli of the materials used were close to the elastic moduli of the surrounding bone to avoid a bone process called stress shielding. Wolff's law states that "Every change in the function of a bone is followed by certain definite changes in its internal architecture and its external conformation." In other words, bone reproduces in accordance to the stresses and strains subjected to it. If extremely strong materials are used in the design, the implant takes over part of the load normally subjected to the bone. The presence of an extremely strong implant results in the growth of weaker bone cells, which can lead to implant loosening.

Motion Constraints:

Designs were chosen to allow the implant to move sufficiently through plantar flexion and dorsiflexion to allow for normal, comfortable gait. According to the Standard Specification for Total Ankle Replacement Prosthesis, ASTM F2665-09, the tibial and talar components must allow a minimum of 15 degrees of dorsiflexion and 15 to 25 degrees of plantar flexion. Motion constraints will lead to a challenge in the design process due to the complex movement involving muscles, ligaments, and bone/ankle movement. For the beginning design stages, focus was aimed toward ankle movement.

Size of the Prosthesis/Dimensions:

The position of the prosthesis in the body and how that relates to the overall comfort and maneuverability of the patient was contemplated and analyzed. It can be very beneficial for the contacting surfaces between components to remain congruent throughout entire gait cycle. Additionally, increasing contact area between the tibial and talar components will decrease stress concentrations by distributing load more evenly across the implant. Two existing implants, the Scandinavian Total Ankle Replacement and the Buechal-Pappas TAR, have contact surface areas of about 600 mm². This value served as the contact surface area goal for some exemplary embodiments.

Maximum Load Capacity:

Load capacity of the prosthesis was determined by the materials used, geometry of the design, and the stresses the design can withstand. The maximum load capacity of the prosthesis then determines the demographic with which the implant can be used. A maximum weight of 250 pounds was tested using finite element analysis.

Surgical Impact:

Ease of installation and removal of bone during installation are also two major concerns. One of the biggest causes of implant failure is malalignment during installation. Overly intricate designs can prove more difficult to install, increasing the chances of failure. The manipulation and removal of bone is ideally kept to a minimum to uphold bone integrity and avoid creating weak spots or extreme stress concentrations around the implant.

Environmental Constraints

The environmental constraints not only include how the prosthesis affects the natural surroundings, but how the prosthesis affects the biological system of the patient. Embodiments of the prosthesis design were installed into a biological system, so the compatibility of the materials with the body tissue and the toxicity of those materials were greatly considered. The feasibility of the design is directly related to the body's acceptance of the implant. Materials used in the design ideally must not cause harm or illness to the patient, and emissions related to the production, use, and disposal of the implant are ideally not harmful to the environment.

Budget Constraints

A major factor in deciding to have such an implant installed in the body is cost. Designs ideally therefore use cost-effective materials and are less intricate geometries in order to improve functionality and longevity while reducing costs of production and installation. Current prosthesis designs on the market are believed to average about $8,900 for the Salto Talaris™ by Tornier to roughly $15,000 for the INBONE™ TAR by Wright. In some disclosed embodiments, the cost of the new design of disclosed embodiments was comparable; in the $8,000-$10,000 range.

Inverted Design Alternative

Disclosed embodiments utilize an inverted design as compared to conventional ankle replacement prosthesis. As such, ankle replacement prostheses according to the disclosed embodiments include a tibial component which attaches to a patient's tibia and provides a convex bearing surface and a talar component which attaches to the patient's talus and provides a concave bearing surface configured to interface with the convex bearing surface of the tibial component to provide a joint of the ankle replacement prosthesis. In conventional designs, the tibial component provides the concave bearing surface, while the talar component provides the convex bearing surface.

One resulting inverted implant alternative can be seen in FIGS. 1-6. This inverted design of an ankle replacement prosthesis 100 includes two components, the talar component 110 on the bottom and the tibial component 120 on the top. The talar component includes the concave bearing surface 428 of the prosthesis (see e.g., FIGS. 4 and 5), while the tibial component 120 includes the convex bearing surface 128.

In exemplary embodiments, various materials can be used for talar component 110 and tibial component 120. For example, in some exemplary embodiments, the tibial component and talar component comprise carbon-fiber-reinforced (CFR) polyetheretherketone (PEEK). Further, in some exemplary embodiments, while the talar component 110 and the tibial component 120 are formed from CFR PEEK, the bearing surfaces of these components comprise ultra-high-molecular-weight polyethylene (UHMWPE). In addition to performing well as a total ankle replacement prosthesis, these materials provide the added advantage of not setting off metal detectors. This is advantageous in that total ankle replacement prosthesis have conventionally caused problems for recipients who must go through airport or other screening.

Figure 2:
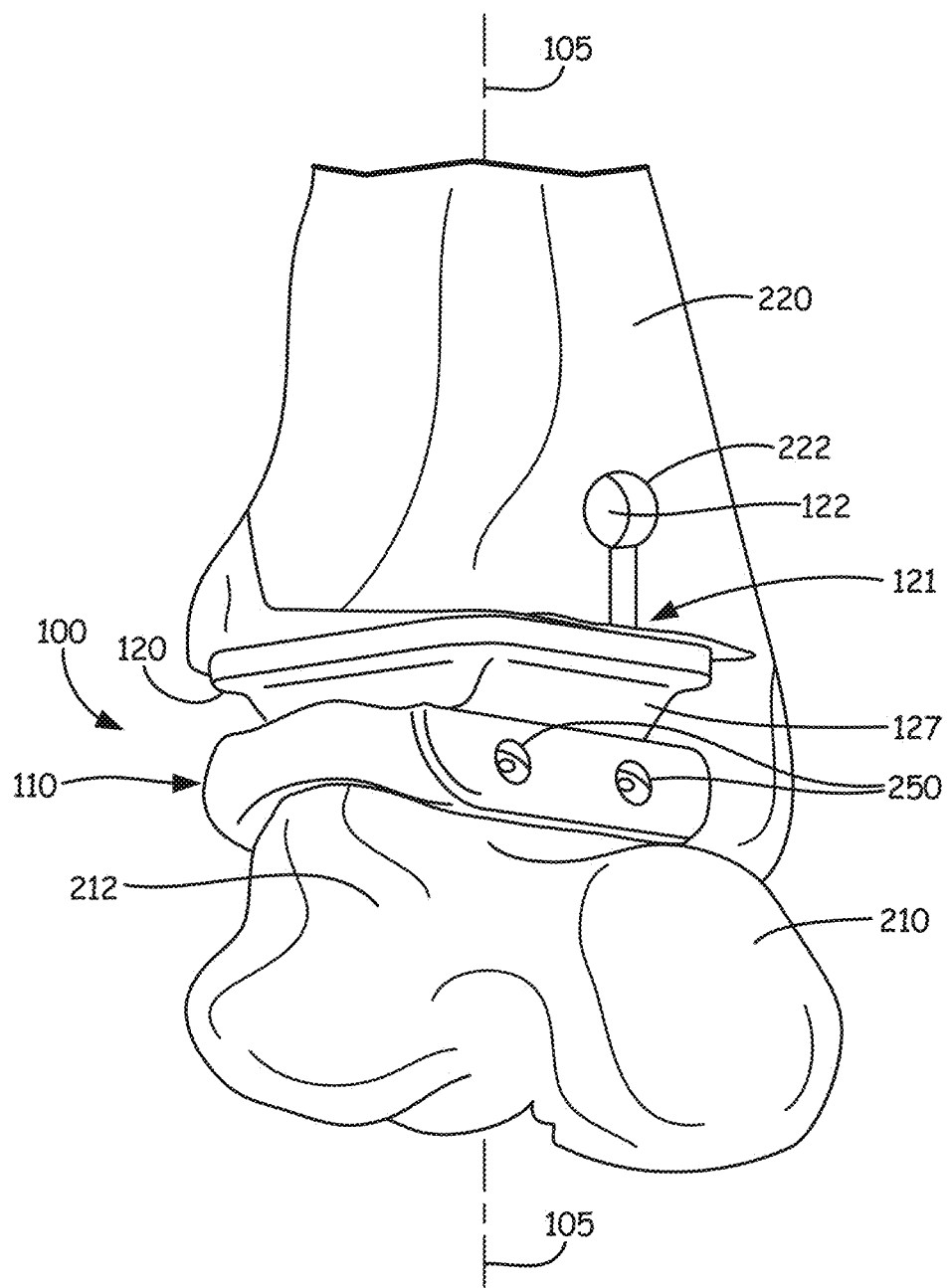
FIG. 2 is a perspective view of the prosthesis shown in FIG. 1 implanted in a patient.
Figure 3:
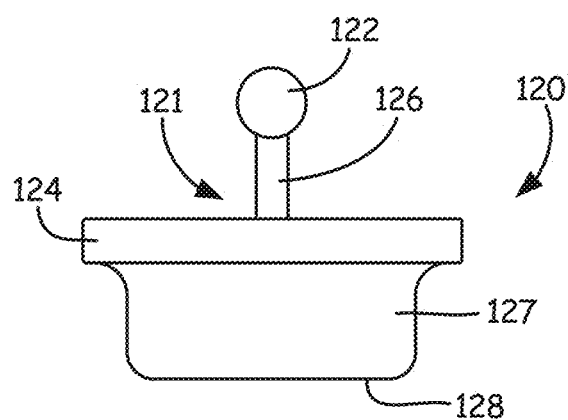
FIG. 3 is a view of a tibial component of the TAR prosthesis.

In exemplary embodiments, the tibial component 120 includes a tibial bearing component 127 providing the convex bearing surface 128 and a tibial attachment component 121 configured to be attached to the patient's tibia 220 (see e.g., FIG. 2). Tibial bearing component 127 and tibial attachment component 121 can be integrally formed as a single continuous material. In some exemplary embodiments, tibial attachment component 121 includes a cylinder 122, a base portion 124, and a support portion or stem 126 extending between the base portion and the cylinder. The cylinder 122 extends in a first direction 123 shown in FIG. 1. The first direction can be, in exemplary embodiments, orthogonal to an axis of loading 105 which extends down through the prosthesis 100. FIG. 3 illustrates side views of two example tibial components 120 of differing dimensions, in which the first direction in which the cylinders 122 extend is illustrated to be into the plane of the page.

As shown in FIG. 2, the cylinder 122 is configured to be inserted into slot 222 cut into the patient's tibia 220. Typically, an incision is made on the front of the patient's ankle, slot 222 is cut in the bone, and the cylinder is inserted anteriorly to posteriorly into the tibia to attach the tibial component to the tibia. As will be shown in detail with reference to a second embodiment, the cylinder member 122 can include one or more cross apertures which extend in a direction which is either orthogonal to the first direction 123, or which has a directional component which is orthogonal to the first direction 123, to allow bony ingrowth of the tibia into the cylinder member 122 once inserted into the tibia.

Figure 4:
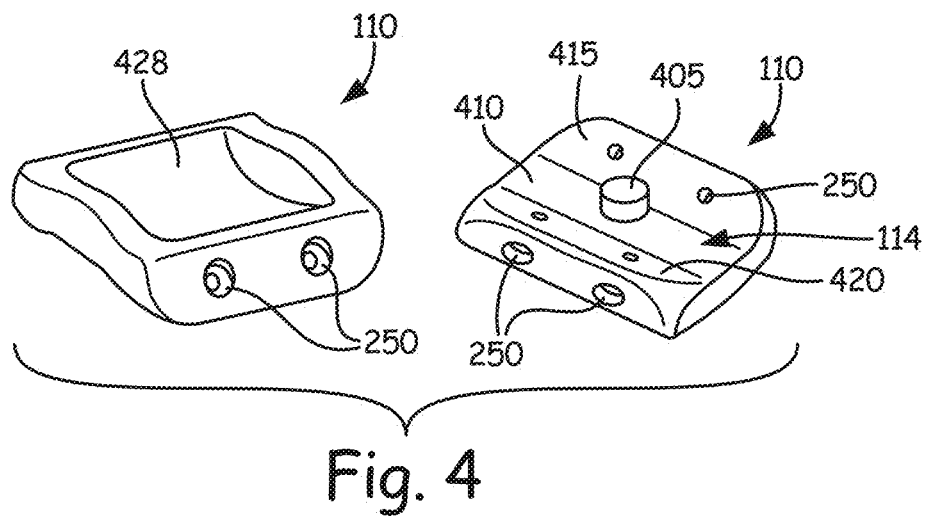
FIGS. 4-6 are views of a talar component of the TAR prosthesis.
Figure 5:
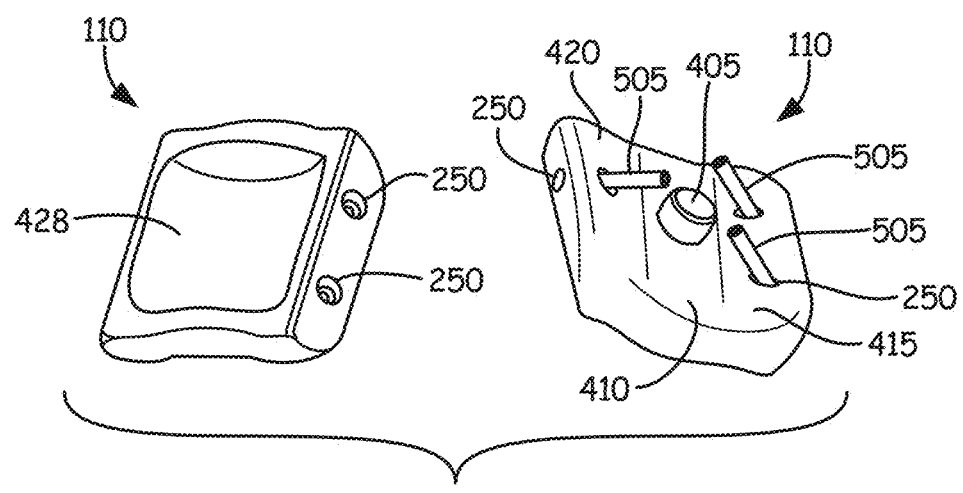
Figure 6:
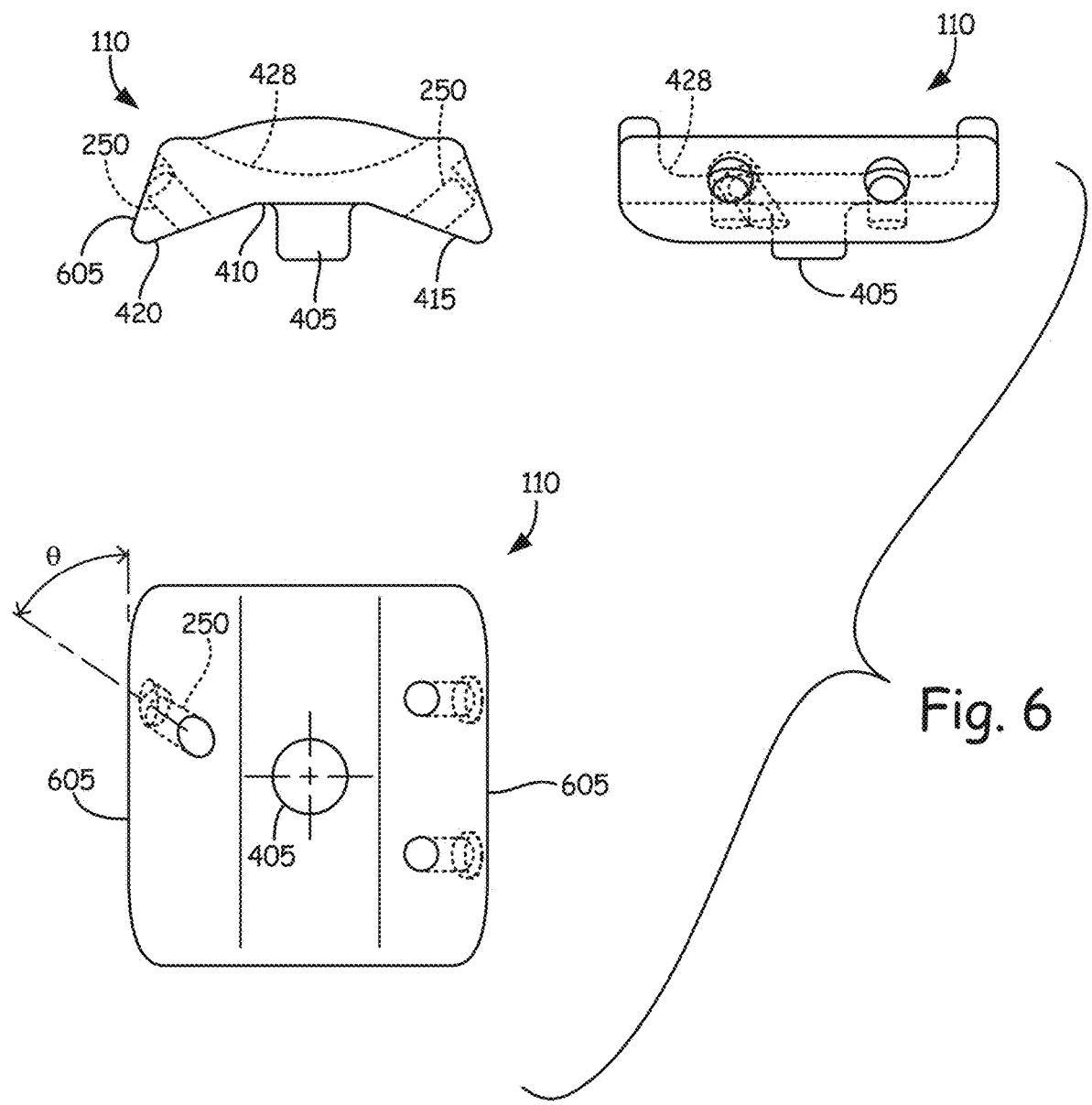

The talar component 110 shown in FIGS. 1, 2, 4 and 5 features a flat angled bottom 114 to allow for easier surgery. It has been concluded that flat, angled surfaces 114 are much easier for surgeons to cut into the bone than curved surfaces. As shown in FIGS. 4 and 5, each of which illustrates a top perspective view of the bearing surface 428 of talar component 110 on the left hand side, and each of which illustrates a bottom perspective view of the talar component 110 on the right hand side, shows that talar component 110 includes a mounting post 405 positioned on a middle flat surface 410, while bottom surfaces 415 and 420 are angled relative to middle flat surface 410. Also illustrated in FIGS. 2, and 4-6 are a plurality of screw receiving apertures 250 formed in the talar component 110 and each disposed and arranged on the talar component to receive a corresponding one of a plurality of screw fasteners 505 (shown in FIG. 5) to attach the talar component 110 to the patient's talus 210. FIG. 4 illustrates a four screw design, while FIGS. 5 and 6 illustrate a three screw design. In some embodiments, at least one of the plurality of screw receiving apertures is disposed and arranged so as to direct the corresponding one of the plurality of screw fasteners 505 toward the talar neck 212 of the patient's talus, in order to maximize screw length. As shown in the bottom view in the lower left of FIG. 6, screw receiving apertures are formed in flat edge portions 605 of component 110, and at least one of the screw receiving apertures is disposed at an angle θ relative to the flat edge portion 605 of between 50 degrees and 60 degrees. In one example embodiment, angle θ is approximately 55 degrees. The angle is chosen to aim or direct the corresponding screw 505 from posterior to anterior toward the talar neck 212, thus allowing maximized or longer screw length to better attach the talar component 110 to the talus 210. The talar component 110 is concave in the middle, but around the edges it is flat. The angle θ is relative to the flat portion of the edges 605 that makes up a transverse plane. The angle θ of the screw receiving aperture relative to the side 605 of the talar component 110, is also the same angle of the screw receiving aperture relative to the bone cut in the talus. In other words, angle θ is relative to the flat interface between the talar component 110 and the talus 210.

One goal of our inverted designs is to keep the components as simple as possible to manufacture and analyze. A simple design allows for less intricate finite element analysis, simpler manufacturing, and to act as a cornerstone for future design improvements. A complicated geometry will increase the analysis time and cause more errors which will more likely create inaccurate results. Also, with a simple design manufacturing is less complicated; thus, price and manufacturing time is reduced. Design improvements can easily be added to a less complicated design providing steps at which to optimize features more accurately.

Two-Component Design Modifications

In exemplary embodiments, both talar and tibial components underwent design changes to further improve the prosthesis. First, in some embodiments the previously conventional use of two holding pins of the talar component were deemed too small and too susceptible to stress. Another concern was the overall attachment of the talar component to the talus. It was believed that a metallic, porous coating and hydroxyapatite may not be enough to hold the component in place. To correct this issue, designs featuring a larger center post 405, four screw holes (FIG. 4), and three screw holes (FIGS. 5 & 6) were analyzed. Second, the four sharp corners of previous embodiments were rounded to better conform to the talus. The resulting design can be seen in top and bottom views of the talar component (FIG. 5).

The design was well accepted with a small change regarding the screw holes or apertures 250. The hole on the anterior (front) side of the implant was reduced to just one at an angle θ to allow for easier insertion of the screw between the ligaments and from the incision site. This final talar design can be seen in FIG. 4.

Special 3 mm solid core screws 505 are used in exemplary embodiments. Screws with a length of 14 mm were deemed sufficient for attachment to the talus. Both titanium alloy and stainless steel options are available.

The tibial component 120 of the two-component design also underwent small changes. The barrel or cylinder 122 diameter was increased from 5 mm to 7 mm and the width of the stem 126 was increased from 2 mm to 3 mm. Later prototypes showed these design changes improve the robustness of the barrel and stem. Prototyping is further discussed in the section Rapid Prototyping.

Various barrel styles were developed and analyzed. In an exemplary embodiment, a cylindrical barrel 122 with four 3.5 mm diameter cross holes or apertures 725 (see e.g., FIG. 7) was used. The cross holes or apertures 725 extend in a direction with a directional component which is orthogonal to the first direction 123 in which the barrel or cylinder 122 extends. This barrel type was found to withstand the stress levels adequately through finite element analysis and could be made through a simple secondary operation during manufacturing. The purpose of the holes is to allow bone ingrowth creating a stronger connection between the tibia and tibial component.

With the discussed design changes, the amount of bone required to be resected was estimated using CAD software to be 4,856 $mm^2$ and 16,024 $mm^2$ for the talus and tibia, respectively.

Hybrid Design Alternative

One possible reason for failure of prostheses that was found throughout the reviewed literature was the loosening of the components due to small rotation around the vertical axis of the ankle. This was especially a problem in constrained two-component designs. Three-component designs allow for free rotation through a mobile bearing; however, there have been observed issues with too much freedom of a mobile bearing. In some disclosed embodiments, we introduce a new concept that meets in the middle of constrained two-component and mobile bearing three-component designs. This "hybrid" design features a bearing that was allowed to rotate, yet be fixed to the tibial component.

Two main hybrid designs out of four concepts were analyzed. The first was a snap-fit design. The second featured two tabs that allowed for the bearing to be connected to the tibial component when rotated at an angle of 90 degrees. These designs featured the same talar component 110 discussed above, but a two sub-component tibial component 520. These components and the overall design can be seen in FIGS. 7-12.

The other two concepts were determined to not be optimal due to high stress points and since they are only held together by compressive forces. The two-component and snap-fit designs were analyzed using finite element analysis and are discussed more thoroughly. Further, the snap-fit and tabbed designs were rapid-prototyped for better observation and analyses of the components.

Figure 7:
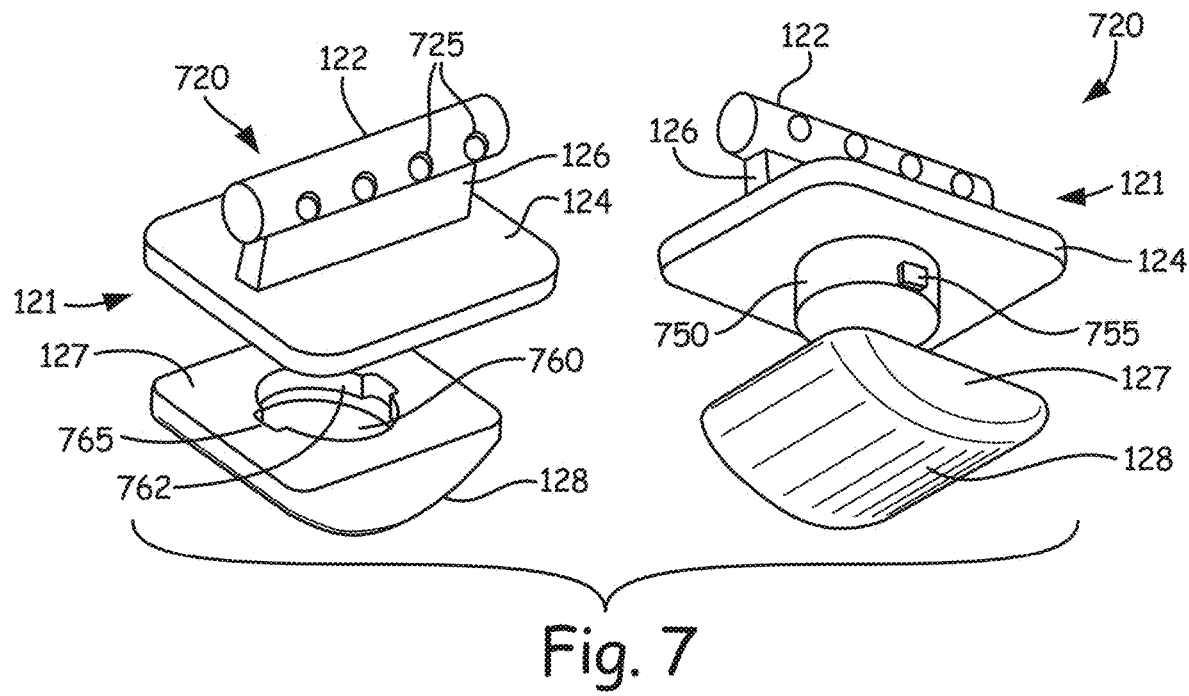
FIG. 7 shows perspective views of an alternate tibial component embodiment of the TAR prosthesis.
Figure 8:
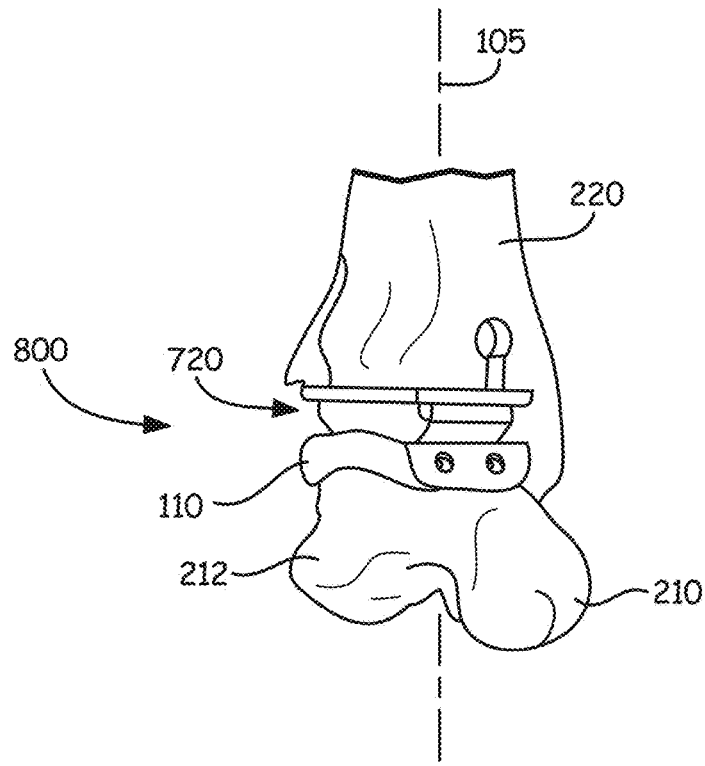
FIG. 8 is a perspective view of a TAR prosthesis, having an alternate tibial component embodiment, implanted in a patient.

Referring now more specifically to FIG. 7, shown is tibial component 720, which is similar to tibial component 120 discussed above, but includes a separate tibial bearing component 127 and tibial attachment component 121 that are configured to be pivotably or rotatably secured to one another. In one example embodiment, pivotal attachment is achieved by including a post or cylinder 750 on the bottom of base portion 124 of tibial attachment component and a receiving aperture 760 in tibial bearing component 127. The post or cylinder 750 includes tabs 755 which align with tab receiving area 765 on the sides of aperture 760. This allows for the tibial bearing component 127 to be connected to the tibial attachment component 121 when rotated at an angle of 90 degrees, for example. In other embodiments, the degrees of rotation for attachment of the tibial bearing component to the tibial attachment component can be in accordance with design preferences and need not be 90 degrees. A lip or channel 762 of the aperture 760 prevents cylinder 750 from being unintentionally removed from aperture 760, while allowing rotation or swiveling of tibial components 121 and 127 relative to each other after implanting of the prosthesis to emulate natural lateral motion of an ankle. The rotation or swiveling of these two tibial sub-components relative to each other is about the axis of loading 105 of the prosthesis 800 shown in FIG. 8. The in-toeing (adduction) and out-toeing (abduction) can be minimal, for example only about 12 degrees total at the level of the ankle in some embodiments. Lack of this motion in some conventional TAR prostheses increases stress on adjacent joints and within the prosthesis and surrounding bones and tissues. In some disclosed embodiments which maintain this rotational motion, stress on the prosthesis, other joints, and surrounding bones and tissues is reduced.

Figure 9:
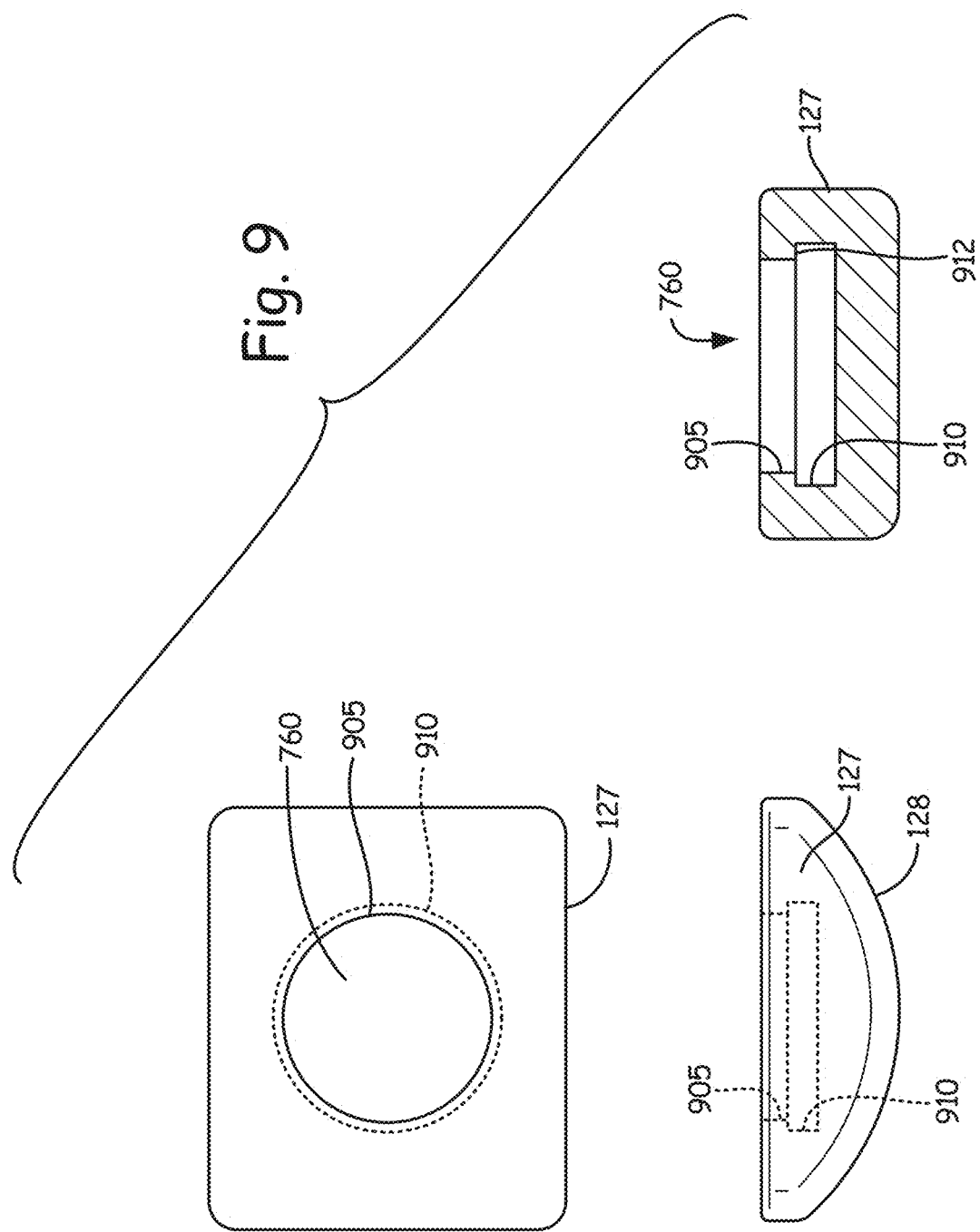
FIGS. 9 and 10 are views, respectively, of a tibial bearing component and a tibial attachment component of yet another alternate tibial component embodiment.
Figure 10:
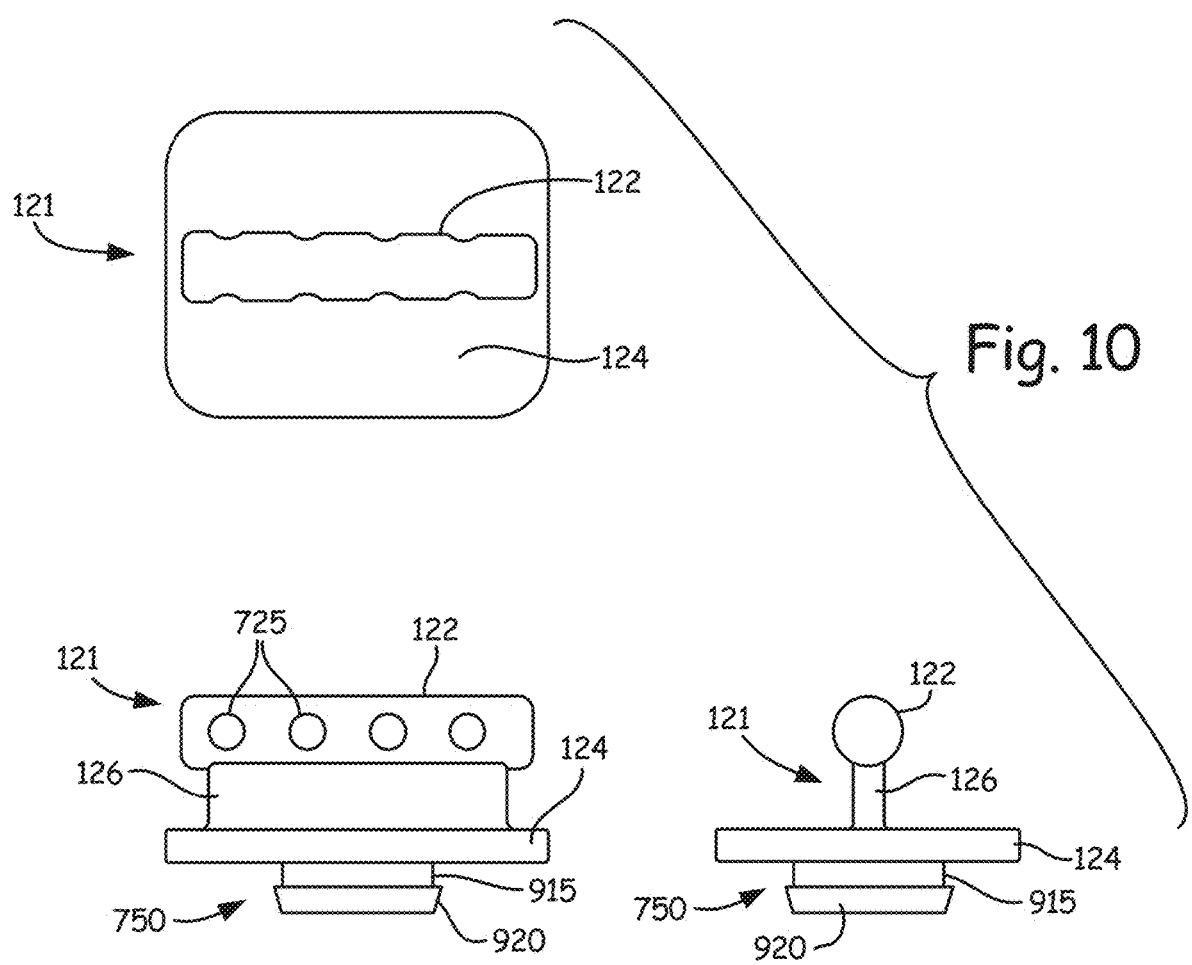

Referring now to FIG. 9, shown is another embodiment of tibial bearing component 127 utilizing a snap fit design to attach component 127 to tibial attachment component 121. Here, instead of a tabbed design, aperture 760 has at its entrance a first or smaller diameter area 905, and then beyond the entrance a second or larger diameter area 910. A lip or retaining surface 912 is defined between areas 905 and 910. FIG. 10 illustrates the corresponding snap fit design for tibial attachment component 121. As can be seen in the side and end views at the bottom of FIG. 10, post or cylinder 750 has a first or larger diameter portion 920 and a second or smaller diameter portion 915. Once post or cylinder 750 is snapped into aperture 760 of tibial bearing component 127, larger diameter portion 920 is retained in aperture 760 by lip or retaining surface 912.

Figure 11:
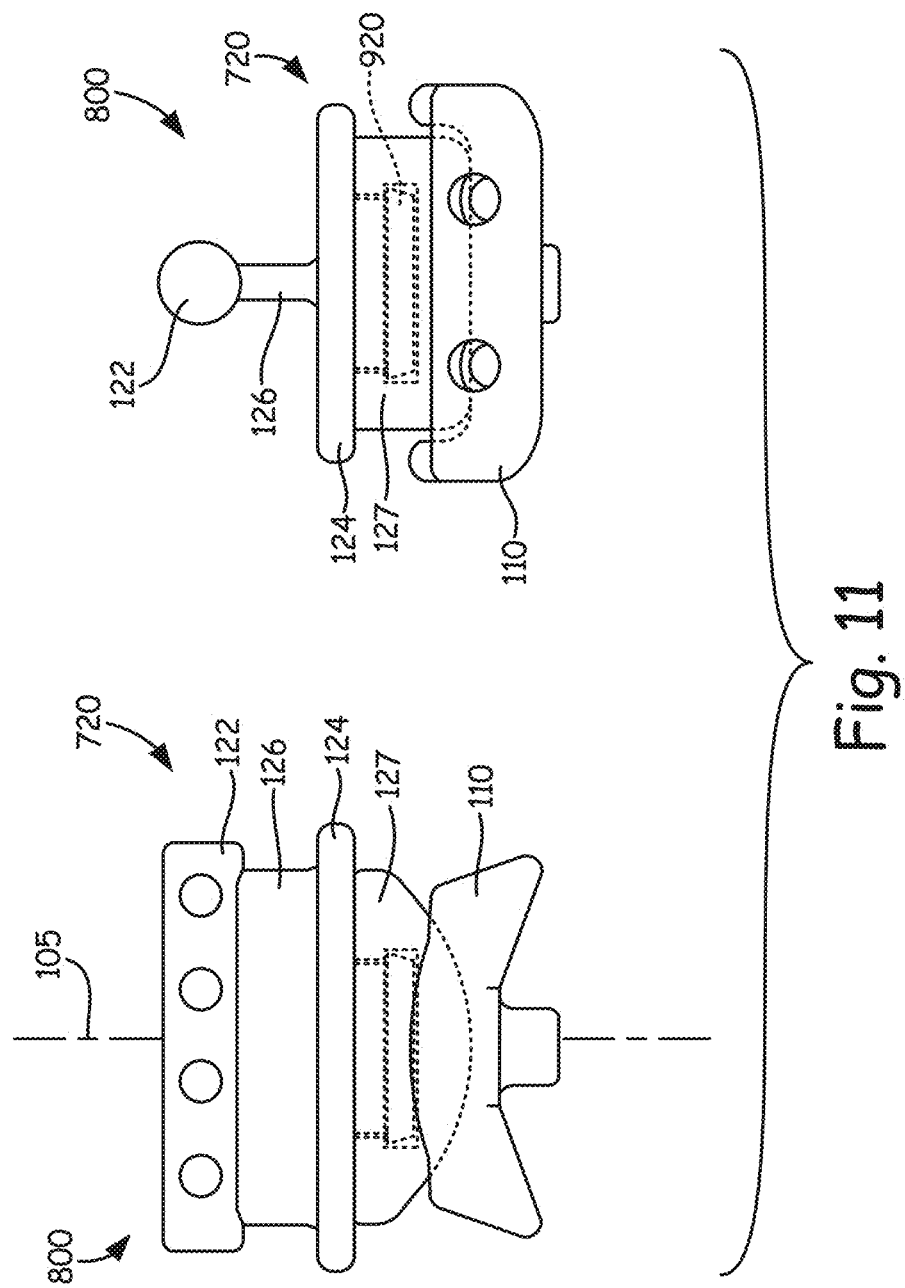
FIGS. 11 and 12 are views of the tibial component embodiment including the tibial bearing component and the tibial attachment component of FIGS. 9 and 10.
Figure 12:
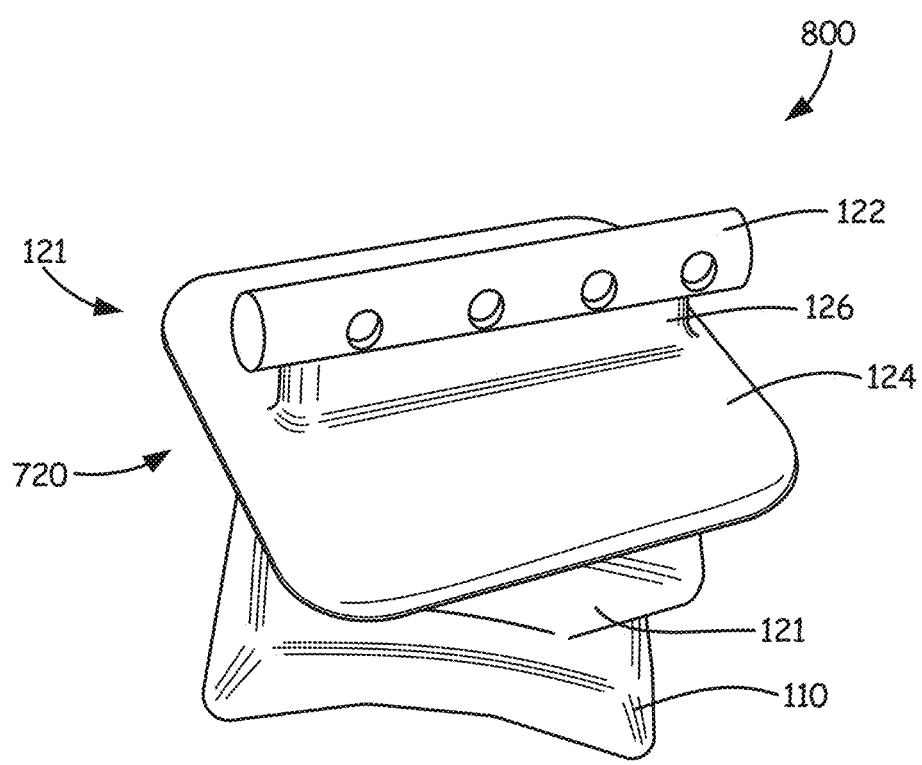

The resulting ankle replacement prosthesis 800 shown in the side and end views of FIG. 11 is very similar or the same in appearance to prosthesis 100 shown in FIG. 1 and corresponding figures, but the tibial attachment component 121 will be able to rotate relative to the tibial bearing component 127 about the axis of loading 105. FIG. 12 illustrates prosthesis 800 with tibial attachment component 121 in a partially rotated state relative to tibial bearing component 110.

Hybrid Design

A hybrid design was developed because it introduces a new concept in TAR performance. After careful consideration of each hybrid alternative, the snap fit design was chosen for further analysis and development. However, other designs without the snap fit are contemplated and are considered to fall within the scope of the present invention. It was believed that the snap fit design would have the least stress occurring at the tibial-bearing connection and finite element analysis showed it to withhold the applied force of 4500 N. Additionally, there would be no chance of the bearing and tibial component separating as in the case of two of the alternatives.

The hybrid design includes three components allowing for more material combinations. The combinations being considered for the final design ranging from most conventional to most non-conventional are as follows:
Option A: CoCrMo Tibial Component—UHWMPE Bearing—CoCrMo Talar Component
Option B: CoCrMo Tibial Component—PEEK Bearing—CoCrMo Talar Component
Option C: PEEK Tibial Component—PEEK Bearing—PEEK Talar Component
The Tibial Component refers to the tibial attachment component 121, the Bearing refers to the tibial bearing component 127, and the Talar Component refers to talar component 110.

Finite Element Analysis

Introduction

Finite element analysis for the disclosed embodiments was focused on improving the understanding of the forces on the ankle prosthesis. The analysis was elementary in the fact that all analysis was done to identify the stress distribution in the prosthesis, which complimented the design process. Consequently, the results were also elementary and drew few conclusions to validate both the design and material selection. After completing previous analysis it was decided to improve the current analysis, and the conclusion was to include forces from tendons, apply a more accurate force distribution and more accurately control the constraints. It was determined that the forces from the tendons were on a much smaller scale than the forces applied directly to the ankle during walking; thus, these forces were ignored in further analysis. To improve the force distribution and control the constraints, the bones obtained from CT scans were included in the assembly for analysis. Commercially available computer aided drafting (CAD) and finite element analysis (FEA) software packages were used in the design of all embodiments. Analysis of the following design and material selections are as follows:
1. 2 Component design (FIGS. 13 & 14)
a. Invibio Motis™ CFR PEEK tibial component on CoCrMo talar component.
b. Invibio Motis™ CFR PEEK tibial component on Invibio Motis™ talar component.
2. Hybrid design (FIGS. 15 & 16)
a. CoCrMo tibial component, UHMWPE bearing, and CoCrMo talar component.
b. CoCrMo tibial component, Invibio Motis™ CFR PEEK bearing, and CoCrMo talar component.
c. Invibio Motis™ CFR PEEK tibial component, Invibio Motis™ CFR PEEK bearing, and Invibio Motis™ CFR PEEK talar component.
All of the analysis combinations were run with the bones modeled as cortical bone. The material and mechanical properties of all of the materials can be seen in Table 1 included in FIG. 17.

Procedure

Geometry files were created for each design at 0 degrees, 5 degrees plantarflexion and dorsiflexion, 10 plantar and dorsiflexion, and 15 degrees plantarflexion and dorsiflexion using CAD software. Two sets of geometry files were created; one without the inclusion of bones and the other with bones. Both were done to compare the stress distributions. The geometry files were then ready for FEA. For the analysis with bones, a body sizing mesh of 2.5 mm was applied to the talus and the tibia bones while a smaller body sizing mesh (between 1.15 mm and 1.4 mm) was applied to the prosthesis components to fulfill the maximum allotted 250,000 nodes within 20,000 nodes. An evenly distributed force of 4500 N was applied to the top of the tibia pointing towards the talus, and the bottom of the talus was simulated as a fixed support. All contact surfaces along the assembly were modeled as bonded connections. For the analysis without bones, the same procedure was applied except the bones were not present. The analysis was solved for the equivalent Von-Mises stress.

Results

The following results display the localized Von-Mises stress for the prosthesis. The stress was higher due to the stress located on the titanium screw. The stress for the following results was measured at the maximum point along the contact surfaces.

Hybrid-No Bones

Figure 15:
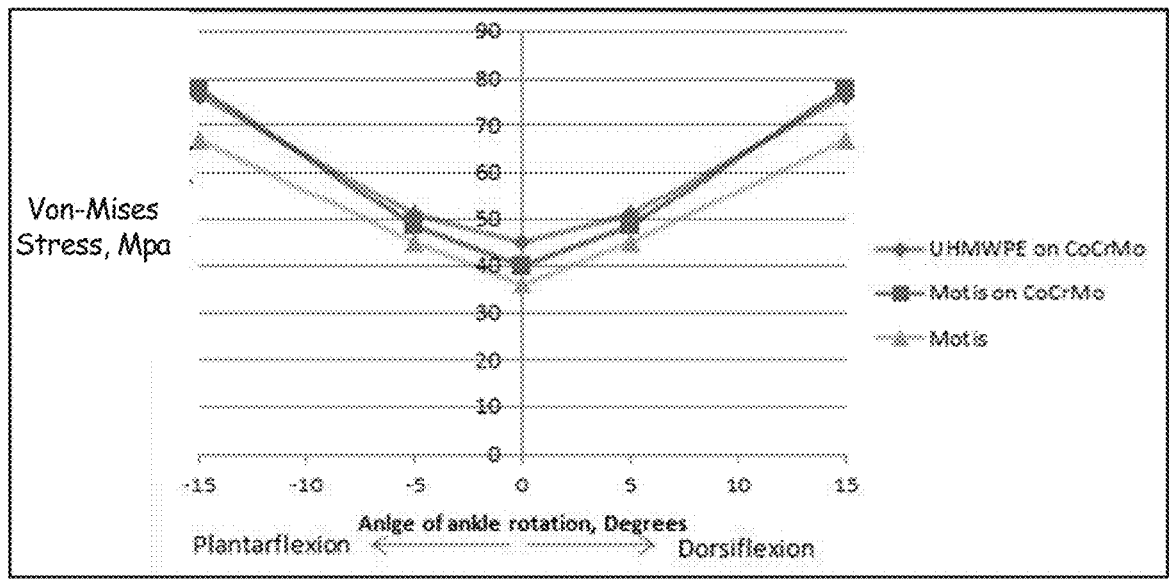

As can be seen in FIG. 15, the stress on the prosthesis without bones is symmetric for all angles of dorsiflexion and plantarflexion. This is to be expected since the prosthesis is symmetrical and the force applied was distributed evenly. The max stress for all material selection occurs at 15 degrees for the Motis™ on CoCrMo combination while the lowest stress occurs at 0 degrees for the Motis™ on Motis™ material combination. These values are 78.04 MPa and 36.34 MPa respectively. The max stress for the Motis on Motis combination and the UHMWPE on CoCrMo combination are 67.01 MPa and 76.2 MPa respectively.

Hybrid—with Bones

Figure 16:
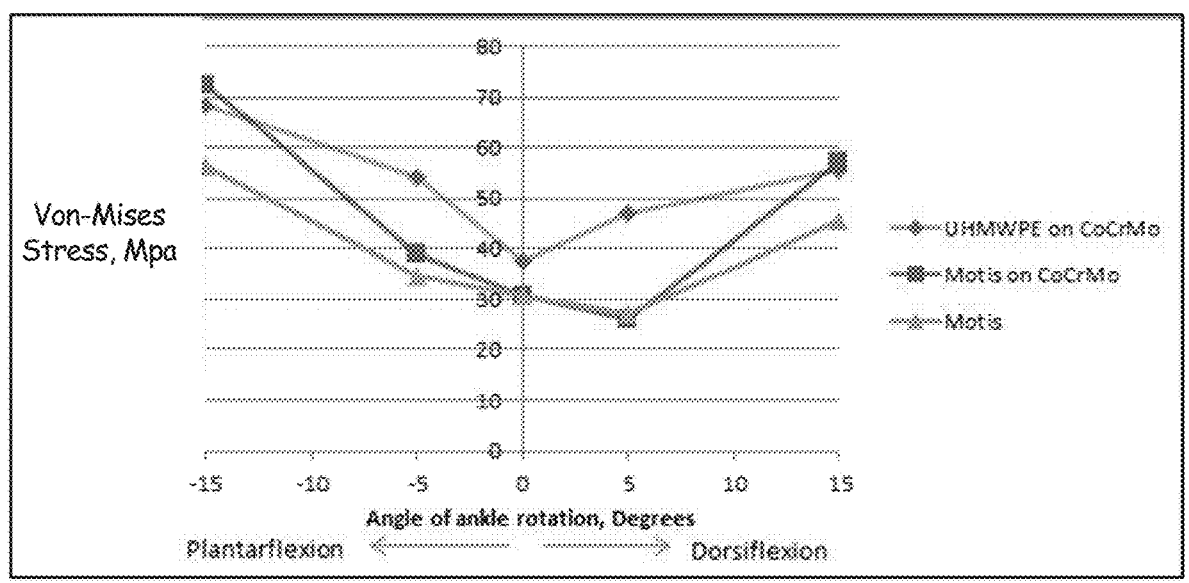

The analysis that was run with the bones yielded a non-symmetrical result for gait from dorsiflexion to plantarflexion. Again, this is to be expected since the bones are non-symmetrical themselves, and the force distributed through the bones was not even. As seen in FIG. 16, the highest stress occurs at 15 degrees plantarflexion for the Motis™ on CoCrMo material combination and the lowest value occurs at 0 degrees of rotation for the all Motis™ material combination. These values are 72.55 MPa and 30.65 MPa respectively. The max values for each material occurs during 15 degrees plantarflexion, and plantarflexion values are higher than comparable dorsiflexion values.

Two Component—No Bones

Figure 13:
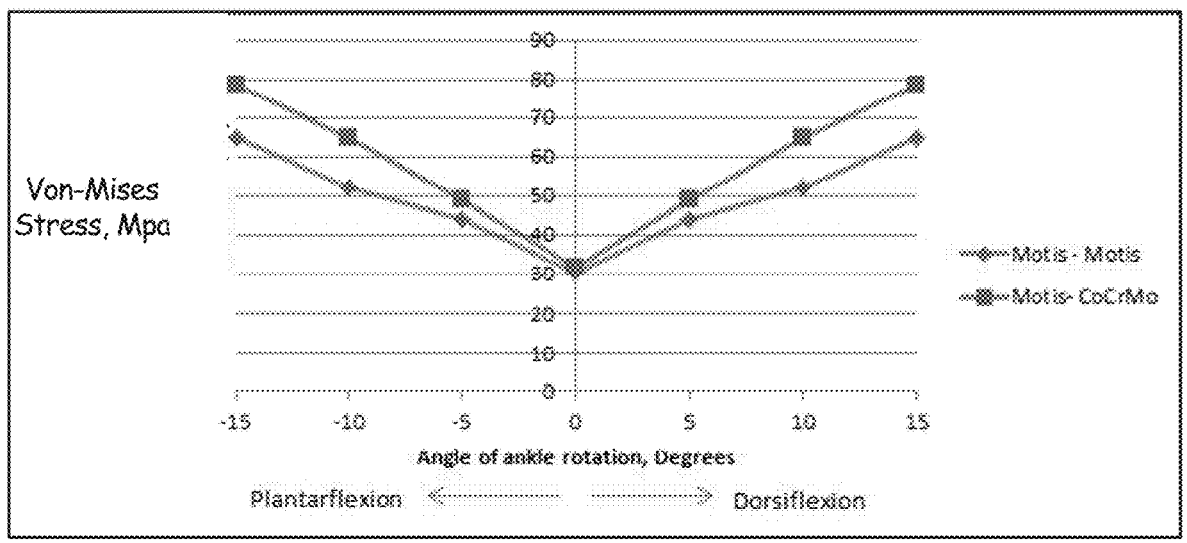
FIGS. 13-16 are graphs illustrating Von-Mises stresses for two component and hybrid designs of the TAR prostheses.

Similar to the hybrid analysis with no bones, FIG. 13 illustrates the symmetric nature of the stress distribution from 15 degrees plantarflexion to 15 degrees dorsiflexion. The combination of Motis™ on CoCrMo yields higher stress values. The max Von-Mises stresses for the Motis™ on CoCrMo material combination and the all Motis™ material combination are 78.64 MPa and 64.87 MPa respectively.

Two-Component—with Bones

Figure 14:
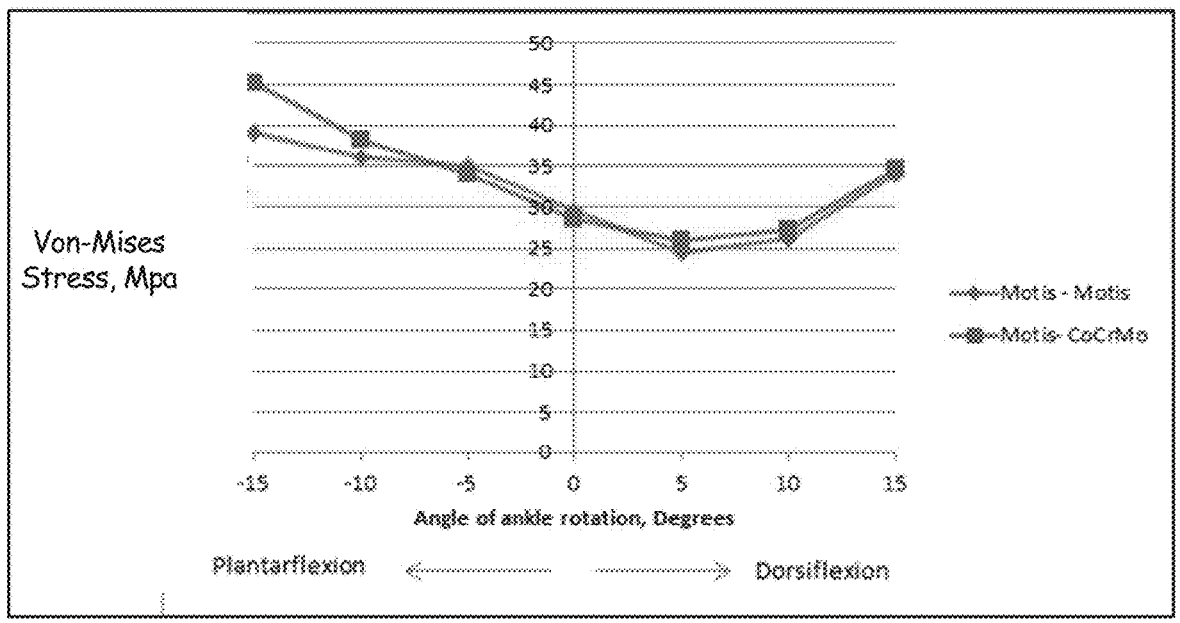

As can be seen in FIG. 14, both material combinations have relatively close values from 15 degrees dorsiflexion to 10 degrees plantarflexion. The greatest deviation in stress occurs at 15 degrees plantarflexion. The highest stress values for the Motis on CoCrMo material combination and the all Motis combination are 45.2 MPa and 39.13 MPa respectively.

CONCLUSIONS

Comparisons of the analysis without bones and with bones not only illustrate the differences in symmetry, but the difference in max Von-Mises stress. For both cases, the analysis without bones yielded higher stress at each point. The analysis with bones yielded lower results due in part to the bones absorbing the stress. That being said, it can also be determined that the bones contribute to the lack of symmetry in the analysis. In terms of yield strength, Motis™ and CoCrMo were well below with their yield strengths being 155 MPa and 1290 MPa respectively. The yield strength of UHMWPE is between 38.6 and 48.3 MPa; thus, the UHMWPE bearing failed for both 5 and 15 degrees in both plantar flexion and dorsiflexion. While not conclusive, the purpose of this analysis was to understand the effect of the bones on the prosthesis in a worst case loading scenario. From this analysis it was found that the stress distribution through the bones is not symmetric and the bones absorb some of the stress from the prosthesis.

Rapid Prototyping

Prosthesis components modeled in a CAD software were converted to ".stl" files and then uploaded into software to be read for rapid prototyping. This specific model uses fused deposition modeling, in which melted plastic is applied in layers to build the part. The entire system is enclosed in an oven chamber to control the process. The nozzle is just above the plastics melting temperature and the surrounding air temperature is below the melting temperature so that the plastic hardens almost immediately after being extruded from the nozzle. The advantages to this type of prototyping are the ability to us ABS plastic, parts can be made relatively fast, and complex parts can be made. On average it took about 15 hours for each batch of prototypes to be produced. The disadvantages to fused deposition modeling are secondary operations are required to remove support material and the parts produced have poor surface finishes.

First Prototype Production

Three separate batches of prototypes were produced. The first prototypes included two two-component assemblies, two snap-fit hybrid assemblies, one full un-cut ankle, and one cut ankle to accommodate both implant designs.

The motion of the designs was as desired. The snap-fit connection was found to be too tight. Some sanding of the connection was required for the components to fit together. The two talar posts were immediately deemed to be too small and weak as well as the tibial stem and barrel. Design modifications discussed above were made to account for these faults.

Second Prototype Production

The second batch of prototypes included the modified two-component design discussed, the tabbed hybrid design, one cut talus, and one cut tibia. The design modifications showed a dramatic improvement in robustness of features in both the tibial and talar components. The screw holes were also determined to be a modification that would be included in the final design.

Disclosed embodiments include multiple novel concepts. The shape of the disclosed TAR designs can be used to maximize surface area in contact at all points of motion to provide better stress distribution. Another novel concept includes the snap fit of the tibial bearing component into the tibial attachment component which allows better degree of motion than with strictly a traditional 2 component design, but at the same time is fixed to the tibial attachment component. Another novel aspect of some disclosed embodiments includes fixation of the talar component to the bone in how it is not just done with bony ingrowth, but is also achieved with screws to afford greater stabilization. Yet another novel feature of some disclosed embodiments includes fixation of the tibial component with a shorter barrel design with one or more cross holes to allow bony ingrowth as opposed to long stems found on other TARs in the market.

Further still, the integration of different materials provides novel features in some embodiments, which has led to at least the following options for exemplary designs:

A. CoCrMo tibial component, UHMWPE bearing, and CoCrMo talar component

B. CoCrMo tibial component, CFR PEEK bearing, and CoCrMo talar component

C. CFR PEEK tibial component, CFR PEEK bearing, and CFR PEEK talar component

Yet another novel feature can include the smooth shape and contours of each component to require little bone to be removed during surgery and less stretching/navigation of the surrounding tendons which allows quicker surgery and faster rehabilitation time.

Although the present invention has been described with reference to preferred embodiments, workers skilled in the art will recognize that changes may be made in form and detail without departing from the spirit and scope of the invention. As used herein, a bearing or a bearing component can be considered to include weight bearing components and/or components that provide bearing surfaces that are in contact but slide or move relative to one another. Individual components can also provide both bearing functions in some instances. For example, a tibial bearing component can be weight bearing and provide a tibial bearing surface which interfaces and moves relative to a talar bearing component. Other bearing components can slide, pivot or rotate relative to each other.

What is claimed is:

1. An ankle replacement prosthesis, comprising:
a tibial component comprising a tibial bearing component providing a convex bearing surface and a tibial attachment component configured to be attached to a patient's tibia, the tibial bearing component and the tibial attachment component configured to be secured to one another by a pivotal attachment that allows pivoting or rotation between the tibial bearing component and the tibial attachment component relative to each other after implanting of the ankle replacement prosthesis to emulate natural lateral motion of an ankle, wherein the pivotal attachment comprises:
a post on the tibial attachment component;
an aperture in the tibial bearing component and configured to receive the post;
a snap-fit connection including a lip formed in the aperture and configured to snap-fit the post into the aperture and to allow pivoting or rotation between the tibial bearing component and the tibial attachment component about an axis of loading, the axis of loading being parallel to a direction the post is snap-fitted into the aperture; and
a talar component configured to be attached to the patient's talus, the talar component providing a concave bearing surface configured to interface with the convex bearing surface of the tibial component to provide a joint of the ankle replacement prosthesis, the talar component comprising:
a top portion defining the concave bearing surface;
a bottom portion configured for fixation to the patient's talus, the bottom portion having:
a flat bottom surface arranged opposite the concave bearing surface;
a mounting post extending from the flat bottom surface; and
anterior and posterior angled bottom surfaces arranged adjacent to the flat bottom surface and at an angle with respect to the flat bottom surface;
flat edge portions extending from posterior and anterior sides of the top portion to the bottom portion, the flat edge portions and the anterior and posterior angled bottom surfaces defining anterior and posterior fastening flanges; and
a plurality of screw receiving apertures each configured to receive a screw fastener, wherein at least one screw receiving aperture extends through the posterior fastening flange in a posterior to anterior direction to direct at least one of the plurality of screw fasteners toward a talar neck of the talus.

2. The ankle replacement prosthesis of claim 1, wherein the tibial component further comprises a cylinder member extending in a first direction and configured to be inserted into the patient's tibia, the cylinder member having at least one aperture or opening to allow bony ingrowth of the tibia into the cylinder member of the tibial component.

3. The ankle replacement prosthesis of claim 1, wherein the tibial component and talar component comprise carbon-fiber-reinforced (CFR) polyetheretherketone (PEEK) and wherein the bearing surfaces of the tibial component and the talar component comprise ultra-high-molecular-weight polyethylene (UHMWPE).

4. The ankle replacement prosthesis of claim 1, wherein the aperture of the pivotal attachment has a first aperture diameter at an aperture entrance, and a second aperture diameter, larger than the first aperture diameter, beyond the aperture entrance, the lip providing a retaining surface formed between the aperture entrance and aperture areas having the second aperture diameter, and wherein the post has a first portion having a first post diameter and a second portion having a second post diameter, smaller than the first post diameter, wherein when the post is fully received in the aperture to allow pivoting or rotation between the tibial bearing component and the tibial attachment component, the first post portion is retained in the aperture by the retaining surface of the lip.

5. The ankle replacement prosthesis of claim 1, wherein the post of the pivotal attachment is positioned on a bottom of a base portion of the tibial attachment component, and wherein the aperture is positioned in the tibial bearing component.

6. The ankle replacement prosthesis of claim 1, wherein the at least one screw receiving aperture that extends through the posterior fastening flange extends at an angle between 50 degrees and 60 degrees relative to the flat edge portion of the posterior fastening flange.

7. The ankle replacement prosthesis of claim 1, wherein the at least one screw receiving aperture that extends through the posterior fastening flange extends at an angle of 55 degrees relative to the flat edge portion of the posterior fastening flange.

8. The ankle replacement prosthesis of claim 1, wherein two screw receiving apertures extend through the anterior fastening flange in an anterior to posterior direction.

9. The ankle replacement prosthesis of claim 8, wherein the two screw receiving apertures that extend through the anterior fastening flange exit the anterior angled bottom surface at opposite sides of the mounting post.

10. The ankle replacement prosthesis of claim 9, wherein the at least one screw receiving aperture that extends through the posterior fastening flange exits the posterior angled bottom surface in a direction toward the mounting post.

11. The ankle replacement prosthesis of claim 1, wherein the post has a cylindrical shape that includes a first diameter portion and a second diameter portion, the first diameter portion being larger than the second diameter portion;
wherein the aperture has a circular shape that includes a first diameter area and a second diameter area, the second diameter area being larger than the first diameter area; and wherein the lip snap-fits the post into the aperture by capturing the first diameter portion of the post in the second diameter area of the aperture.

12. An ankle replacement prosthesis comprising:

a tibial component comprising a tibial bearing component providing a convex bearing surface and a tibial attachment component, the tibial bearing component and the tibial attachment component configured to be secured to one another by a pivotal attachment that allows pivoting or rotation between the tibial bearing component and the tibial attachment component relative to each other, wherein the pivotal attachment comprises:
   a post on the tibial attachment component having a larger diameter portion and a smaller diameter portion;
   an aperture in the tibial bearing component configured to receive the post; and
   a snap-fit connection including a lip formed in the aperture, the snap-fit connection configured to snap-fit the post into the aperture in a direction parallel to an axis of loading and to allow pivoting or rotation between the tibial bearing component and the tibial attachment component about the axis of loading, wherein the lip of the snap-fit connection is configured to retain the larger diameter portion of the post in the aperture; and a talar component comprising:
   a top portion comprising:
      a concave bearing surface configured to interface with the convex bearing surface of the tibial component to permit anterior and posterior pivoting of the talar component relative to the tibial component to provide a joint of the ankle replacement prosthesis; and
      sidewalls adjacent to the concave bearing surface to limit side-to-side movement of the talar component relative to the tibial component;
   a bottom portion configured for fixation to a talus, the bottom portion comprising:
      a flat bottom surface arranged opposite the concave bearing surface;
      a mounting post extending from the flat bottom surface; and
      anterior and posterior angled bottom surfaces arranged adjacent to the flat bottom surface, and projecting at an angle away from the flat bottom surface;
   flat edge portions extending along anterior and posterior sides of the talar component and extending from the top portion to the bottom portion of the talar component, wherein the flat edge portions and the anterior and posterior angled bottom surfaces define anterior and posterior fastening flanges;
   first and second screw receiving apertures extending through the anterior fastening flange from the flat edge portion at the anterior side of the talar component to the anterior angled bottom surface of the talar component, the first and second screw receiving apertures being spaced apart from each other and extending in an anterior to posterior direction; and
   a third screw receiving aperture extending through the posterior fastening flange from the flat edge portion at the posterior side of the talar component to the posterior angled bottom surface of the talar component, the third screw receiving aperture being disposed at an angle relative to the flat edge portion at the posterior side of the talar component of between 50 degrees and 60 degrees and extending in a posterior to anterior direction.

13. The ankle replacement prosthesis of claim 1, further comprising a plurality of screw fasteners, wherein a screw fastener received by the third screw receiving aperture that extends through the posterior fastening flange is directed toward a talar neck.

* * * * *